(12) United States Patent
Dickhans et al.

(10) Patent No.: US 12,193,733 B2
(45) Date of Patent: Jan. 14, 2025

(54) INFLOW AND OUTFLOW CONTROL OF A CLOSED COOLING SYSTEM

(71) Applicant: Covidien LP, Mansfield, MA (US)

(72) Inventors: William J. Dickhans, Longmont, CO (US); Jiagui Li, Shanghai (CN); Zhiwei Lin, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/460,756

(22) Filed: Sep. 5, 2023

(65) Prior Publication Data

US 2023/0404666 A1     Dec. 21, 2023

Related U.S. Application Data

(63) Continuation of application No. 16/493,054, filed as application No. PCT/CN2017/076392 on Mar. 13, 2017, now Pat. No. 11,759,257.

(51) Int. Cl.
*A61B 18/18* (2006.01)
*A61B 18/00* (2006.01)

(52) U.S. Cl.
CPC ........ *A61B 18/1815* (2013.01); *A61B 2018/00023* (2013.01); *A61B 2018/00577* (2013.01)

(58) Field of Classification Search
CPC ...... A61B 18/1815; A61B 2018/00023; A61B 2018/00577
See application file for complete search history.

(56) References Cited

U.S. PATENT DOCUMENTS

| 9,119,650 B2 | 9/2015 | Brannan et al. |
| 11,759,257 B2 * | 9/2023 | Li .................. A61B 18/1815 606/33 |

(Continued)

FOREIGN PATENT DOCUMENTS

| CN | 201701613 U | 1/2011 |
| CN | 102846376 A | 1/2013 |

(Continued)

OTHER PUBLICATIONS

International Search Report issued in corresponding Appl. No. PCT/CN2017/076392 mailed Dec. 20, 2017 (4 pages).

(Continued)

*Primary Examiner* — Ronald Hupczey, Jr.
(74) *Attorney, Agent, or Firm* — Carter, DeLuca & Farrell LLP

(57) ABSTRACT

A microwave ablation antenna assembly including a coaxial cable terminating in a radiating section, a first tubular member circumscribing the coaxial cable and spaced therefrom to permit fluid flow therebetween, and a second tubular member circumscribing the first tubular member and spaced therefrom to permit fluid flow therebetween. The microwave ablation antenna assembly further includes a hub configured to receive the coaxial cable, first tubular member, and second tubular member, the hub including a fluid inflow chamber and a fluid outflow chamber and an integrated hub divider and hub cap separating the fluid inflow chamber from the fluid outflow chamber and prohibiting fluid flow between the inflow chamber and outflow chamber except via the spacing between the coaxial cable and the first tubular member and between the first tubular member and the second tubular member.

20 Claims, 4 Drawing Sheets

(56) References Cited

U.S. PATENT DOCUMENTS

| | | | |
|---|---|---|---|
| 2011/0295245 A1 | 12/2011 | Willyard et al. | |
| 2013/0237982 A1 | 9/2013 | Rencher et al. | |
| 2014/0276739 A1* | 9/2014 | Brannan | A61B 34/25 606/33 |

FOREIGN PATENT DOCUMENTS

| | | |
|---|---|---|
| CN | 104042324 A | 9/2014 |
| CN | 104519821 A | 4/2015 |

OTHER PUBLICATIONS

Written Opinion of the ISR issued in corresponding Appl. No. PCT/CN2017/076392 mailed Dec. 20, 2017 (4 pages).
Extended European Search Report issued in corresponding Appl. No. EP 17900843.8 dated Sep. 11, 2020 (9 pages).
European Examination Report issued in corresponding application EP 17900843.8 dated Nov. 25, 2022 (4 pages).

* cited by examiner

INFLOW AND OUTFLOW CONTROL OF A CLOSED COOLING SYSTEM

CROSS-REFERENCE TO RELATED APPLICATIONS

This application is a continuation of U.S. patent application Ser. No. 16/493,054, filed on Sep. 11, 2019, now U.S. Pat. No. 11,759,257, which is a U.S. National Stage Application filed under 35 U.S.C. § 371(a) of International Patent Application No. PCT/CN2017/076392, filed on Mar. 13, 2017.

FIELD

The present disclosure is directed to a water jacketed microwave ablation antenna assembly and more particularly to devices for sealing inflow from outflow of a cooling medium in a hub portion of the microwave ablation antenna assembly.

BACKGROUND

Microwave ablation antennae are a well-known mechanism for treating cancerous lesions and tumors in the body. For example, treatment of liver tumors is often undertaken by the placement of one or more microwave ablation antennae proximate the tumor and then treatment with microwave radiation up to and exceeding 150 W of power for a duration sufficient to coagulate and kill the tissue of the tumor and some margin of healthy tissue.

Some microwave ablation antennae are cooled using compressed or liquefied $CO_2$ gas, which during expansion absorbs energy from the antenna and particularly the coaxial cabling to help limit damage to healthy tissue proximate the radiating section which is normally formed on a distal portion of the antenna. The actual radiator of such devices is often separated from the cooling gas flow.

In an alternative arrangement, a circulating fluid, generally saline or deionized water, is pumped through the microwave ablation antenna assembly. One such configuration has been described in detail in commonly assigned U.S. Pat. No. 9,119,650, entitled "Microwave Energy-Delivery Device and System," to Brannan et al. the entire contents of which are incorporated herein by reference. FIG. 1 depicts a microwave ablation antenna assembly 10 configured for circulating a fluid therethrough. As shown in FIG. 1, the microwave ablation assembly 10 includes a transition 12, which connects via a coaxial cable to a microwave ablation generator (not shown). The transition 12 allows for a 90o change in direction of the coaxial cable entering the transition 12 to the coaxial cable 14 of the microwave ablation assembly 10. The coaxial cable 14 extends perpendicularly from the transition 12 and concludes at a radiating section 16. The radiating section 16 may take many forms including monopole, dipole, symmetric and asymmetric configurations. The coaxial cable 14 extends through a first tubular member 18, which is itself housed within a second tubular member 20. Between the coaxial cable 14 and the first tubular 18 member is a first fluid channel 22 and between the first tubular 18 member and the second tubular member 20 is a second fluid channel 24. The transition 12 is received within a first end of a hub 26, a hub cap 28 is received at a second end of the hub 26, and is itself designed to receive and secure the second tubular member 20. O-rings 30 and 32 formed on the hub cap 28 and the transition 12, form seals creating a watertight compartment 34 therebetween.

Further, as shown in FIG. 1, the watertight compartment 34 is separated into inflow chamber 36 and outflow chamber 38 by hub divider 40. The hub divider 40 receives the first tubular member 18 and maintains it in alignment with the second tubular member 20. The hub divider 40 is formed of an elastomeric material and forms a seal around the first tubular member 18 which, in combination with a compression fit within the hub 26, restricts the egress of fluid in inflow chamber 36 to the first fluid channel 22, and prevents fluid returning through second fluid channel 24 and entering outflow chamber 38 from re-entering the inflow chamber 36. Also shown in FIG. 1 are inflow port 42 and outflow port 44 which connect to inflow chamber 36 and outflow chamber 38, respectively. A wire 48 is depicted extending through the hub 26 and inflow chamber 36 and entering the first tubular member 18 where it will terminate at a point proximate the radiating section 16 and include a thermocouple (not shown) to detect the temperature or the microwave ablation assembly 10. The entire hub 26, hub cap 28, and transition 12, once assembled, are placed within a handle assembly 46 for ease of gripping and other ergonomic concerns.

Though the microwave ablation antenna assembly 10 is quite successful commercially and is currently sold by Medtronic as part of the EMPRINT™ ablation system, improvements are always desirable.

SUMMARY

The present disclosure is directed to a microwave ablation antenna assembly. In accordance with one aspects of the disclosure the assembly includes a coaxial cable terminating in a radiating section, a first tubular member circumscribing the coaxial cable and spaced therefrom to permit fluid flow therebetween, and a second tubular member circumscribing the first tubular member and spaced therefrom to permit fluid flow therebetween. The assembly further includes a hub configured to receive the coaxial cable, first tubular member, and second tubular member, the hub including a fluid inflow chamber and a fluid outflow chamber, a hub divider separating fluid inflow chamber from the fluid outflow chamber, and an inflow tube insert adhered to the inflow tube member and interacting with the hub divider to form a seal prohibiting fluid flow between the inflow chamber and outflow chamber except via the spacing between the coaxial cable and the first tubular member and between the first tubular member and the second tubular member.

In accordance with a further aspect of the disclosure the microwave ablation antenna assembly includes a wall extending from the hub and interfacing with the hub divider to prevent movement of hub divider. Fluid flow is directed from a fluid inflow chamber into the space formed between the coaxial cable and the inner tubular member, and the fluid flow may extend to the radiating section. Further, the fluid flow may return from the radiating section in the spacing between the outer tubular member and the inner tubular member. The microwave ablation antenna assembly may further include a hub cap configured to receive the outer tubular member and be received in the hub to form the outflow chamber.

A further aspect of the present disclosure is directed to a microwave ablation antenna assembly including a coaxial cable terminating in a radiating section, a first tubular member circumscribing the coaxial cable and spaced therefrom to permit fluid flow therebetween, and a second tubular member circumscribing the first tubular member and spaced therefrom to permit fluid flow therebetween. The assembly includes a hub configured to receive the coaxial cable, first tubular member, and second tubular member, the hub including a fluid inflow chamber and a fluid outflow chamber. Still further the assembly includes an integrated hub divider and hub cap separating the fluid inflow chamber from the fluid outflow chamber and prohibiting fluid flow between the inflow chamber and outflow chamber except via the spacing between the coaxial cable and the first tubular member and between the first tubular member and the second tubular member.

In accordance with a further aspect of the present disclosure the microwave ablation antenna assembly includes at least one rib formed on an interior surface of the hub and engaging at least one groove formed on the integrated hub divider and hub cap. The assembly may further include at least one o-ring forming a seal in combination with the integrated hub divider and hub cap to prevent fluid flow between the fluid inflow chamber and the fluid outflow chamber. Fluid flow is directed from a fluid inflow chamber into the space formed between the coaxial cable and the inner tubular member. Fluid flow may extend to the radiating section and may return from the radiating section in the spacing between the outer tubular member and the inner tubular member.

The integrated hub divider and hub cap may include a window fluidly connecting the spacing between the outer tubular member and the inner tubular member with the outflow chamber. The proximal portion of the inner tubular member may be adhered to a proximal portion of the integrated hub divider and hub cap and a proximal portion of the outer tubular member may be adhered to a distal portion of the integrated hub divider and hub cap.

A further aspect of the present disclosure is directed top a microwave ablation antenna assembly including a coaxial cable terminating in a radiating section, a first tubular member circumscribing the coaxial cable and spaced therefrom to permit fluid flow therebetween, and a second tubular member circumscribing the first tubular member and spaced therefrom to permit fluid flow therebetween. The assembly further includes a hub configured to receive the coaxial cable, first tubular member, and second tubular member, the hub including a fluid inflow chamber and a fluid outflow chamber and an integrated hub divider and hub cap separating the fluid inflow chamber from the fluid outflow chamber and prohibiting fluid flow between the inflow chamber and outflow chamber except via the spacing between the coaxial cable and the first tubular member and between the first tubular member and the second tubular member.

In accordance with a further aspect of the present disclosure the assembly includes at least one rib formed on an interior surface of the hub and engaging at least one groove formed on the integrated transition cap and hub divider. The assembly may further include at least one o-ring forming a seal in combination with the integrated transition cap and hub divider to prevent fluid flow between the fluid inflow chamber and the fluid outflow chamber, wherein fluid flow is directed from a fluid inflow chamber into the space formed between the coaxial cable and the inner tubular member.

In accordance with a further aspect of the disclosure, the fluid flow returns to the hub outflow chamber in the spacing between the outer tubular member and the inner tubular member. Further, integrated transition cap and hub divider may include a window fluidly connecting the spacing between the inner tubular member and the coaxial cable with the fluid inflow chamber. Still further, the proximal portion of the inner tubular member may be adhered to a hub divider portion of the integrated transition cap and hub divider.

BRIEF DESCRIPTION OF THE DRAWINGS

Objects and features of the present disclosure will become apparent to those of ordinary skill in the art when descriptions of various embodiments thereof are read with reference to the accompanying drawings, of which.

DETAILED DESCRIPTION

Figure 1:
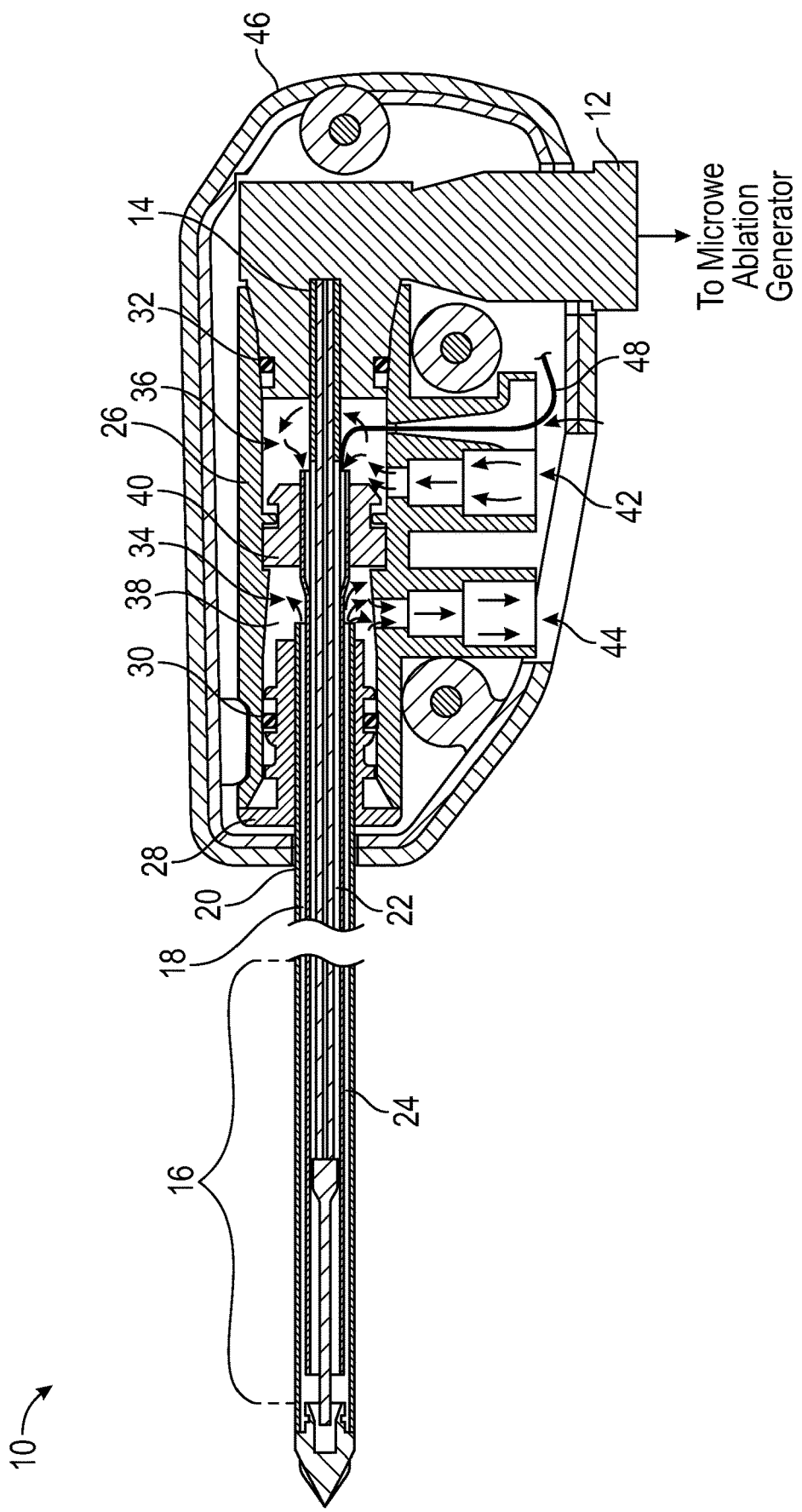
FIG. 1 is a cross-sectional view of a known microwave ablation antenna assembly.
Figure 2:
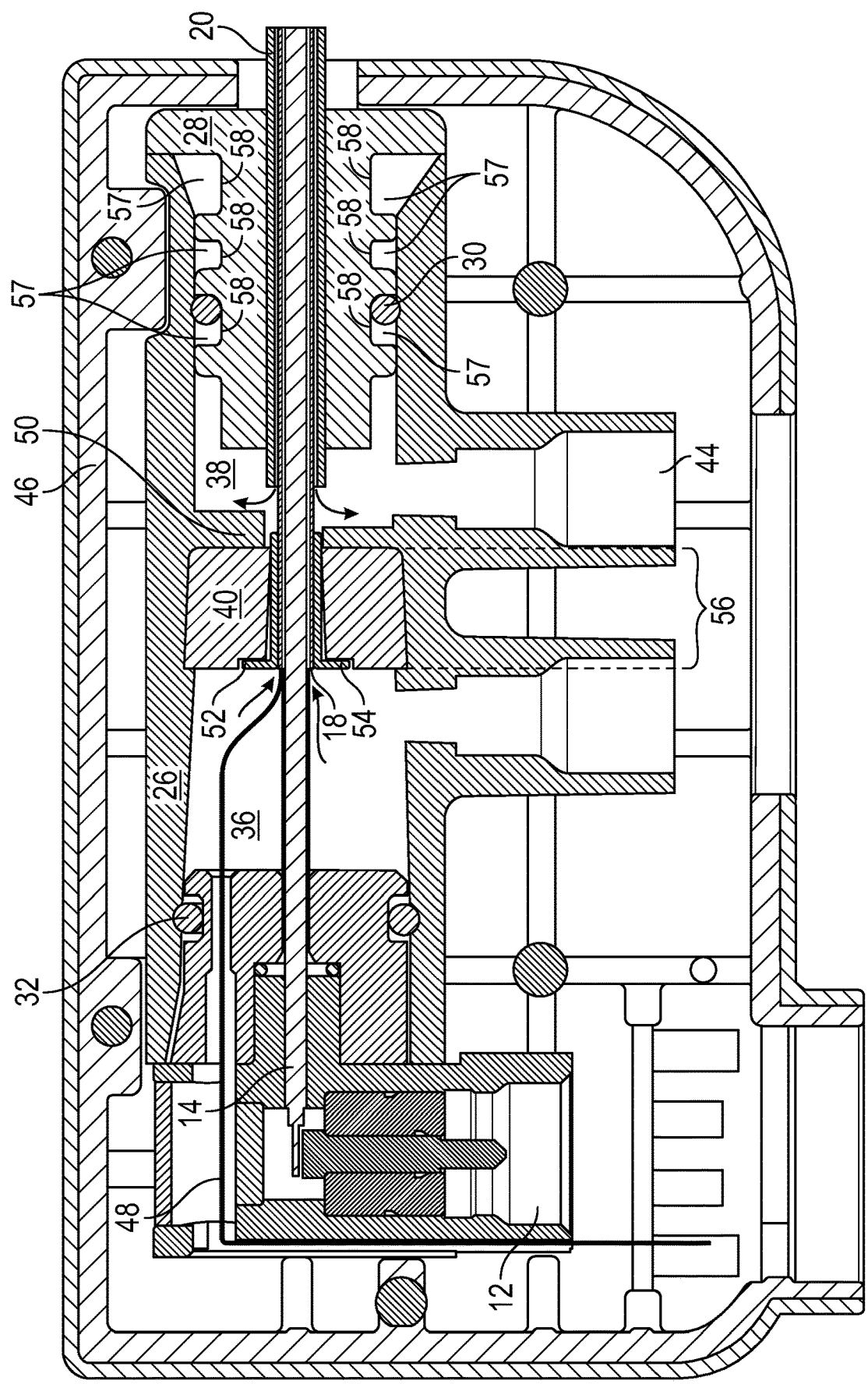
FIG. 2 is a partial cross-sectional view of a microwave ablation antenna assembly according to aspects of the present disclosure.

FIG. 2 depicts a first embodiment of the present disclosure. Handle assembly 46 is depicted enclosing a hub 26. Note common numbering conventions are used where possible amongst all embodiments of the present disclosure. The hub 26 is mated on a first end to a transition 12, which connects a coaxial cable extending to a microwave generator (not shown) to a second coaxial cable 14 at a 90o angle. The transition 12 mates with the hub 26 using an o-ring 32. Extending up through the opening in the handle assembly 46 for receiving the first coaxial cable is a wire 48 which extends into the hub 26 and terminates at a thermocouple (not shown) for sensing the temperature of the microwave ablation assembly 10, and more particularly the temperature proximate the radiating section 16 (FIG. 1).

As depicted in FIG. 2, the hub 26 has a different internal configuration than that depicted in FIG. 1. One difference is the formation of a wall 50 separating the inflow chamber 36 from the outflow chamber 38. In accordance with this embodiment of the present disclosure, an inflow tube insert 52, is received within a hub divider 40. The inflow tube insert 52 includes a flange 54 formed on one end. The flange 54 forms a surface upon which fluid in the inflow chamber 36 acts, and when the inflow chamber 36 is pressurized, compresses the hub divider 40 forming a water tight seal. As a result of this seal between the flange 54 and the hub divider 40, the circulated fluid is forced into the spacing between the first tubular member 18 and the coaxial cable 14. After flowing to the distal portion of the microwave ablation assembly 10, the fluid flows back in the spacing between the first tubular member 18 and the second tubular member 20, to be released into the outflow chamber 38, in much the same fashion as the device shown in FIG. 1. The inflow tube insert 52 may be adhered or bonded (e.g., with a two part adhesive) to first tubular member 18, effectively securing the first tubular member 18 within the handle assembly 46. In addition to the pressure applied to the flange 54 to create a seal between the inflow tube insert 52 and the hub divider 40, the opening in the hub divider 40 through which the inflow tube insert 52 is placed can be sized such that it has a smaller inner diameter than the outer diameter of the inflow tube insert 52. In addition, the outer diameter of the hub divider 40 may be larger than the space 56 within the hub 26 which receives the hub divider 40. The hub divider 40, being made of an elastomeric material, compresses to be received within the space and compresses again to receive the inflow tube insert 52. In this manner fluid is prevented from passing from the inflow chamber 36 to the outflow chamber 38 without first traversing the lengths of the first and second tubular members 18 and 20 respectively. Again a hub cap 28 secures the second tubular member 20 in the hub 26, and may employ an o-ring 30 to prevent fluid flow out of the hub 26 other than out the outflow port 44. Ribs 57 formed on the hub 26 help secure the hub cap 28 by mating with corresponding grooves 58 formed in the hub cap 28.

Figure 3:
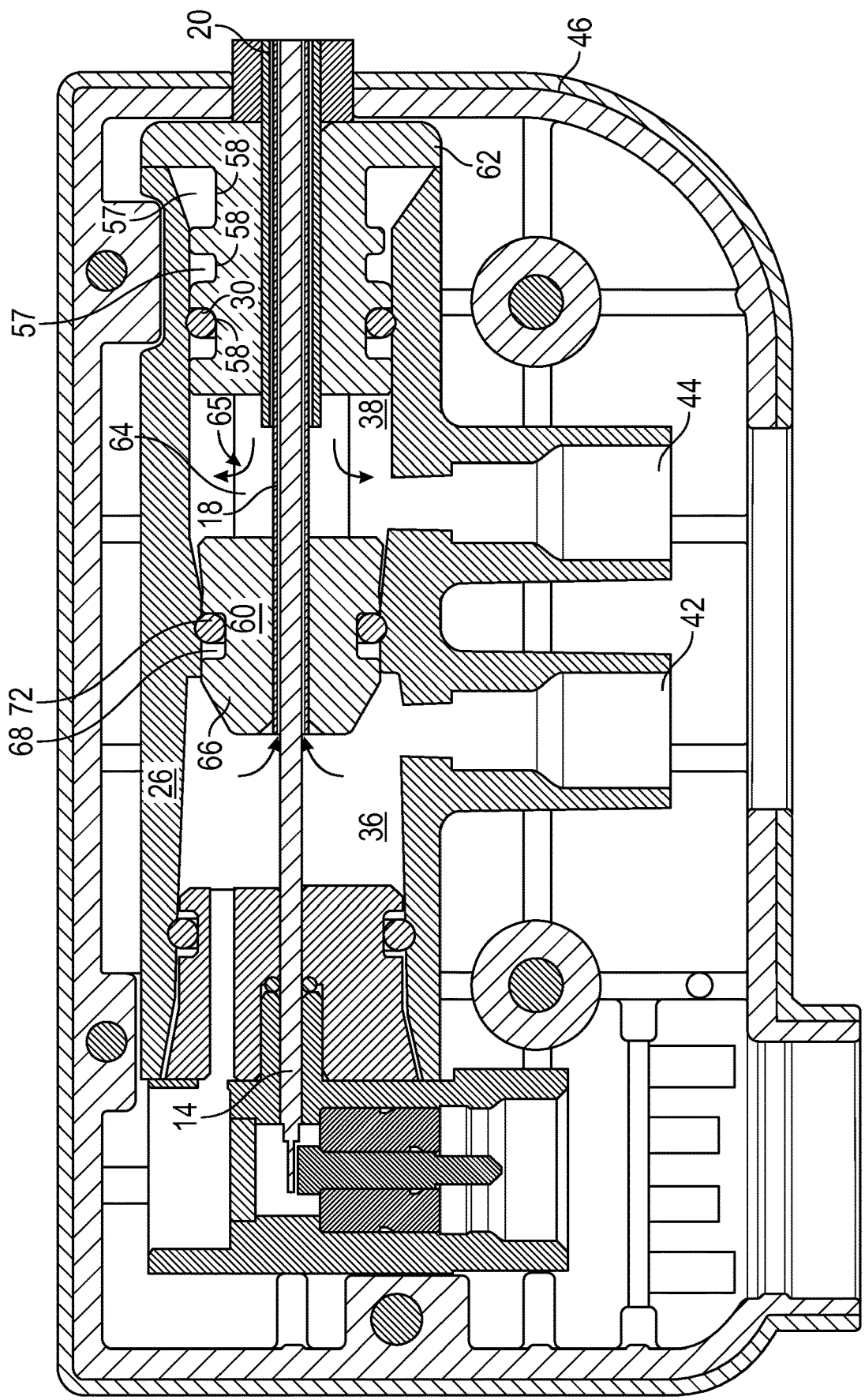
FIG. 3 is a partial cross-sectional view of a microwave ablation antenna assembly according to another aspect of the present disclosure.

FIG. 3 depicts a second embodiment of the present disclosure. The primary difference between the embodiment of FIG. 3 and the embodiment described above in FIG. 2 is again the internal configuration of the hub 26. Unlike the embodiment of FIG. 2, where wall 50 separated the inflow chamber 36 from the outflow chamber 38, in FIG. 3 this separation is formed by an integrated hub divider and hub cap 60. The integrated hub divider and hub cap 60 has a distal portion 62 which is substantially similar to the hub cap 28 shown in FIG. 2. The distal portion 62 is adhered to the second tubular member 20 and forms a seal with the hub 26 in conjunction with ribs 57 and grooves 58 formed on the hub 26 and distal portion 62. To ensure water tight integrity of the seal an o-ring 30 is employed in addition to the grooves 58 and ribs 57. The proximal portion of the second tubular 20 member terminates in an intermediate portion 64 of the integrated hub divider and hub cap 60. The intermediate portion 64 has one or more openings or windows 65 formed therein permitting the flow of fluid from the spacing between the outer tubular member 20 and the inner tubular member 18 and into the out flow port 44.

The intermediate portion 64 of the integrated hub divider and hub cap 60 connects to a proximal portion 66. The proximal portion 66 is secured in the hub 26 by mating ribs 68 formed on an interior surface of the hub 26 with a groove 70 formed in the proximal portion 66. As shown in FIG. 3, an o-ring 72 forms a seal between the proximal portion 66 and the hub 26 which effectively separates the inflow chamber 36 from the out flow chamber 38. The proximal portion 66 is adhered to an outer surface of the first tubular member 18 and in conjunction with the remaining portions of the integrated hub divider and hub cap 60 secure the inner tubular member 18.

Figure 4:
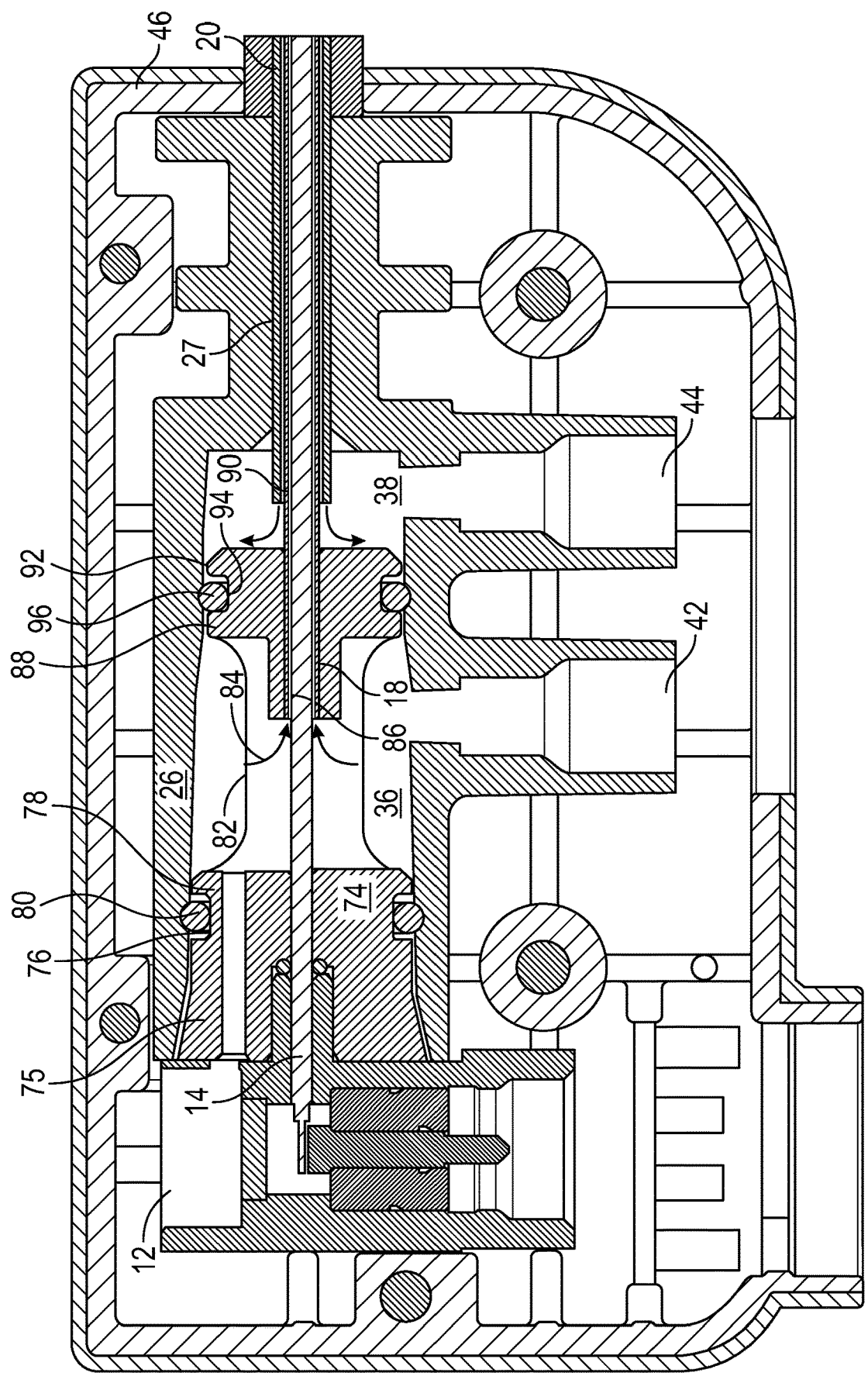
FIG. 4 is a partial cross-sectional view of a microwave ablation antenna assembly according to a further aspect of the present disclosure.

FIG. 4 depicts a further embodiment of the present disclosure. Again one of the main differences is the shape of the hub 26. As depicted, the hub 26 is shaped such that the hub cap 28 is completely eliminated. The outer tubular member 20 may be received in and adhered to a bore 27 formed in a portion of the hub 26. On the opposite end of the handle assembly 46, an integrated transition cap and hub divider 74 connects to the transition 12 and helps hold the coaxial cable 14 in the transition 12. The integrated transition cap and hub divider 74 is formed of three integrated sections. The first is a transition cap 75, which as noted above, secures the coaxial cable 14 in the transition 12. The embodiments of FIGS. 1 and 2 also incorporate transition caps that perform similar functionality but play no role in separating the inflow chamber 36 from the out flow chamber 38, and thus are not described above. As shown the transition cap 75 is secured to the hub 26 by a rib 76 formed on the hub 26 which is received into a groove 78 formed on the transition cap 75. An o-ring 80 prevents fluid from flowing from the fluid inflow chamber 36 out of the handle assembly 46.

Extending from the transition cap 75 is an intermediate portion 82 of the integrated transition cap and hub divider 74. The intermediate portion 82 includes one or more openings or windows 84 permitting fluid to enter the integrated transition cap and hub divider 74 and reach the spacing between the coaxial cable 14 and the inner tubular member 18. The proximal portion of the inner tubular member 18 terminates proximate the window 84. In one embodiment a parallel flange 86 forms a proximal portion of the hub divider portion 88 of the integrated transition cap and hub divider 74. The inner tubular member 18 may be adhered to an inner surface of a bore 90 formed in the hub divider portion 88 of the integrated transition cap and hub divider 74. The hub divider portion 88 is secured to the hub 26 by a rib 92 formed on an inner surface of the hub 26 and a groove 94 formed in the hub divider 88. An o-ring 96 creates a seal between the inflow chamber 36 and the outflow chamber 38.

In accordance with the present disclosure there are several instances described of hub dividers (e.g., 40, 88, and proximal portion 66). Each of these is formed of an elastomeric material and may be adhered to an inner tubular member 18 or inflow tube insert 52 using one or more adhesives. The inner tubular member 18 and inflow tube insert may be formed of a variety of materials including fiberglass, carbon fiber, stainless steel, thermoplastics, other extruded and un-extruded materials, and the like. The adhesives may be selected for their bonding properties for the materials selected as well as their heat resistance as the coaxial cable 14 will become heated during usage. Similar materials and adhesives may be employed for the hub cap 28 and the outer tubular member 20. Further, while the hub 26 is formed of a harder more durable medical grade plastic, in the embodiment of FIG. 4, an adhesive may be chosen for the connecting of the hub 26 to the outer tubular member 20. Similarly, the inflow tube insert 52 in the embodiment of FIG. 2 may be adhered to the wall 50 of the hub 26 by selection of appropriate adhesives.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A microwave ablation antenna assembly, comprising:
a handle assembly;
a coaxial cable extending through the handle assembly;
a hub disposed within the handle assembly and configured to receive the coaxial cable, the hub including a fluid inflow chamber and a fluid outflow chamber;
a hub divider coupled to the hub and separating the fluid inflow chamber from the fluid outflow chamber;
a transition cap coupled to the hub and disposed proximal to the hub divider and the fluid inflow chamber; and
an intermediate tubular member directly coupled to the transition cap and disposed within the fluid inflow chamber between the transition cap and the hub divider.

2. The microwave ablation antenna assembly according to claim 1, further comprising a tubular member circumscribing the coaxial cable and defining a fluid channel between the tubular member and the coaxial cable, wherein the fluid channel is in fluid communication with the fluid inflow chamber.

3. The microwave ablation antenna assembly according to claim 2, wherein the intermediate tubular member includes an opening that places the fluid inflow chamber in fluid communication with the fluid channel.

4. The microwave ablation antenna assembly according to claim 2, wherein a proximal-most end of the tubular member is disposed proximal to a distal-most end of the intermediate tubular member.

5. The microwave ablation antenna assembly according to claim 2, wherein the tubular member and the coaxial cable are received through a bore formed through the hub divider.

6. The microwave ablation antenna assembly according to claim 5, wherein the tubular member is adhered to an inner surface of the bore.

7. The microwave ablation antenna assembly according to claim 1, further comprising a transition disposed within the handle assembly and configured to receive a proximal end portion of the coaxial cable such that the coaxial cable extends through the handle assembly perpendicularly relative to the transition.

8. The microwave ablation antenna assembly according to claim 7, wherein the transition cap secures the coaxial cable within the transition.

9. The microwave ablation antenna assembly according to claim 7, wherein a proximal-most end of the transition cap contacts the transition.

10. The microwave ablation antenna assembly according to claim 1, wherein the intermediate tubular member is out of physical contact with the hub.

11. The microwave ablation antenna assembly according to claim 1, wherein the hub divider includes a proximal end portion disposed proximal to a distal-most end of the intermediate tubular member.

12. A microwave ablation antenna assembly, comprising:
a handle assembly;
a coaxial cable extending through the handle assembly;
a hub disposed within the handle assembly and configured to receive the coaxial cable, the hub including a fluid inflow chamber and a fluid outflow chamber;
a transition disposed within the handle assembly and configured to receive a proximal end portion of the coaxial cable such that the coaxial cable extends through the handle assembly perpendicularly relative to the transition;
a hub divider coupled to the hub and separating the fluid inflow chamber from the fluid outflow chamber; and
a transition cap coupled to the hub and configured to secure the coaxial cable within the transition, the transition cap integrally formed with the hub divider and disposed between the transition and the hub divider such that the fluid inflow chamber is defined between the transition cap and the hub divider.

13. The microwave ablation antenna assembly according to claim 12, further comprising a tubular member circumscribing the coaxial cable and defining a fluid channel between the tubular member and the coaxial cable, wherein the fluid channel is in fluid communication with the fluid inflow chamber.

14. The microwave ablation antenna assembly according to claim 13, wherein the tubular member and the coaxial cable are received through a bore formed through the hub divider.

15. The microwave ablation antenna assembly according to claim 12, wherein a proximal-most end of the transition cap contacts the transition.

16. The microwave ablation antenna assembly according to claim 12, further comprising an intermediate tubular member disposed within the fluid inflow chamber between the transition cap and the hub divider.

17. The microwave ablation antenna assembly according to claim 16, wherein the intermediate tubular member includes an opening that places the fluid inflow chamber in fluid communication with the fluid channel.

18. A microwave ablation antenna assembly, comprising:
a handle assembly including a fluid outflow chamber and a fluid inflow chamber;
a coaxial cable extending through the handle assembly;
a hub divider disposed within the handle assembly to fluidly seal the fluid outflow chamber from the fluid inflow chamber;
a transition cap disposed proximal to the hub divider such that the fluid inflow chamber is defined between the hub divider and the transition cap; and
an intermediate tubular member directly coupled to the transition cap and disposed within the fluid inflow chamber between the transition cap and the hub divider.

19. The microwave ablation antenna assembly according to claim 18, further comprising a tubular member circumscribing the coaxial cable and defining a fluid channel between the tubular member and the coaxial cable, wherein the fluid channel is in fluid communication with the fluid inflow chamber.

20. The microwave antenna assembly according to claim 19, wherein the intermediate tubular member includes an opening that places the fluid inflow chamber in fluid communication with the fluid channel.

* * * * *